(12) United States Patent
Breit et al.

(10) Patent No.: US 7,745,792 B2
(45) Date of Patent: Jun. 29, 2010

(54) TERAHERTZ DETECTORS FOR USE IN TERAHERTZ INSPECTION OR IMAGING SYSTEMS

(75) Inventors: Michael Breit, Munich (DE); Florian Krug, Munich (DE)

(73) Assignee: Morpho Detection, Inc., Newark, CA (US)

(*) Notice: Subject to any disclaimer, the term of this patent is extended or adjusted under 35 U.S.C. 154(b) by 57 days.

(21) Appl. No.: 11/839,375

(22) Filed: Aug. 15, 2007

(65) Prior Publication Data

US 2009/0045343 A1 Feb. 19, 2009

(51) Int. Cl.
G01J 5/02 (2006.01)
(52) U.S. Cl. .................................. 250/341.8
(58) Field of Classification Search .............. 250/341.1
See application file for complete search history.

(56) References Cited

U.S. PATENT DOCUMENTS

| | | | |
|---|---|---|---|
| 3,384,749 A | 5/1968 | Golay | |
| 5,265,470 A | 11/1993 | Kaiser et al. | |
| 5,298,748 A * | 3/1994 | Kenny et al. | 250/338.1 |
| 5,436,452 A * | 7/1995 | Kenny et al. | 250/338.1 |
| 5,449,909 A * | 9/1995 | Kaiser et al. | 250/336.1 |
| 5,710,430 A | 1/1998 | Nuss | |
| 6,078,047 A | 6/2000 | Mittleman et al. | |
| 6,410,912 B1 * | 6/2002 | Villani et al. | 250/252.1 |
| 6,605,808 B2 | 8/2003 | Mickan et al. | |
| 6,815,683 B2 | 11/2004 | Federici et al. | |
| 6,844,552 B2 | 1/2005 | Zhang et al. | |
| 6,909,095 B2 | 6/2005 | Tran et al. | |
| 6,957,099 B1 | 10/2005 | Arnone et al. | |
| 2001/0033636 A1 | 10/2001 | Hartick et al. | |
| 2002/0067480 A1 | 6/2002 | Takahashi | |
| 2002/0074500 A1 | 6/2002 | Mickan et al. | |
| 2004/0155665 A1 | 8/2004 | Arnone et al. | |
| 2005/0156110 A1 | 7/2005 | Crawely | |
| 2006/0022140 A1 | 2/2006 | Connelly et al. | |
| 2006/0056586 A1 | 3/2006 | Uetake et al. | |
| 2006/0111619 A1 | 5/2006 | Castiglione et al. | |
| 2006/0273255 A1 * | 12/2006 | Volkov et al. | 250/336.1 |

(Continued)

FOREIGN PATENT DOCUMENTS

EP 0727671 A2 8/1996

(Continued)

OTHER PUBLICATIONS

Chiko Otani et al.; "Direct and Indirect Detection of Terahertz Waves using a Nb-based Superconducting Tunnel Junction"; 7th European Conference on Applied Superconductivity; Journal of Physics: Conference Series 43 (2006) 1303-1306.

(Continued)

*Primary Examiner*—David P Porta
*Assistant Examiner*—Djura Malevic
(74) *Attorney, Agent, or Firm*—Armstrong Teasdale LLP

(57) ABSTRACT

A technique is provided for examining a subject. The technique includes illuminating at least a part of the subject with THz radiation and detecting THz radiation reflected and/or transmitted from the illuminated part and incident upon a detector array by measuring change in capacitance corresponding to the incident THz radiation.

31 Claims, 4 Drawing Sheets

U.S. PATENT DOCUMENTS

2006/0284774 A1* 12/2006 Salsman ................ 343/703
2008/0156991 A1* 7/2008 Hu et al. ................ 250/341.1

FOREIGN PATENT DOCUMENTS

| GB | 2399626 A | 9/2004 |
|---|---|---|
| GB | 2405263 A | 2/2005 |
| GB | 2411093 A | 8/2005 |
| GB | 2418337 A | 3/2006 |
| WO | WO 00/50859 A1 | 8/2000 |
| WO | WO 2004/072593 A2 | 8/2004 |
| WO | WO2004/083796 A1 | 9/2004 |
| WO | WO2005/080947 A1 | 9/2005 |
| WO | WO 2005/119214 A1 | 12/2005 |

OTHER PUBLICATIONS

J.B Chevrier et al.; "An infrared pneumatic detector made by micromachining technology"; Journal of micromechanics and microengineering, 5 (1995) pp. 193-195.

* cited by examiner

TERAHERTZ DETECTORS FOR USE IN TERAHERTZ INSPECTION OR IMAGING SYSTEMS

BACKGROUND

The invention relates generally to terahertz (THz) detectors and, more specifically, to indirect detection THz detectors for use in THz imaging and/or spectroscopy.

Various imaging and/or inspection modalities have been developed for use in a wide range of medical and non-medical applications. For example, in modern healthcare facilities, non-invasive imaging systems are often used for identifying, diagnosing, and treating physical conditions. Currently, a number of modalities exist for medical diagnostic and imaging systems, each typically operating on different physical principles to generate different types of images and information. These modalities include ultrasound systems, computed tomography (CT) systems, X-ray systems (including both conventional and digital or digitized imaging systems), positron emission tomography (PET) systems, single photon emission computed tomography (SPECT) systems, and magnetic resonance (MR) imaging systems. These various imaging systems, with their different respective topologies, are used to create images or views of a patient based on the attenuation of radiation (e.g., X-rays) passing through the patient. Based on the attenuation of the radiation, the topology of the imaging system, and the type and amount of data collected, different views may be constructed, including views showing motion, contrast enhancement, volume reconstructions, two-dimensional images and so forth. Similarly, a wide variety of imaging and/or inspection systems may be utilized in non-medical applications, such as in industrial quality control or in security screening of passenger luggage, packages, and/or cargo. For example, inspection systems are employed at various public or private installations, such as airports, for screening persons, luggage, packages and cargo, to detect the presence of contraband (e.g., weapons, explosives and drugs). Such systems include metal detectors, X-ray based inspection systems, nuclear magnetic resonance based inspection systems, nuclear quadruple resonance based inspection systems, and so forth. In such applications, acquired data and/or generated images may be used to detect objects, shapes or irregularities which are otherwise hidden from visual inspection and which are of interest to the screener. However, these imaging and/or inspection systems have one or more of various limitations such as low reliability in detecting explosives and drugs (leading to high rates of false alarms), health risk to screeners and those being screened due to exposure to harmful radiation, long screening time (leading to decreased throughput at checkpoints), and so forth.

Electromagnetic radiation in the THz range (about 0.1 THz to 10 THz), or THz radiation, or millimeter waves (MMW), is now being used in the field of contraband detection and other applications such as nondestructive testing, medical imaging, dental imaging, multi-spectral imaging and so forth. THz radiation easily penetrates clothes, cardboard, leather and other non-conductive (non-metallic) materials and poses minimal health risk to subjects being scanned. Moreover, a wide variety of contraband, such as explosives, drugs, chemical and biological agents, and so forth, show strong spectroscopic signatures in the THz range. These unique properties offer significant advantages in the field of contraband detection. However, known THz inspection systems are of limited practical utility because of their high cost and limited range of scanning or imaging. Additionally, known THz inspection systems require lengthy scan times per person or per piece of baggage, thereby reducing the throughput and causing inconvenience to those being screened.

For example, current millimeter wave and/or THz systems employ detectors based on expensive high frequency electronics/components, such as monolithic millimeter integrated circuits (MMIC), that are the cost drivers for the entire system. The key components of these detectors are low noise amplifiers (LNAs) built using MMICs having an operating frequency of about 100 gigahertz (GHz). This further limits the use of current THz systems for applications, which require sub-millimeter resolution such as dental imaging. A common strategy for reducing cost is to reduce the number of channels, thereby reducing the number of LNAs. However, reducing the number of channels makes mechanical scanning necessary, thereby increasing maintenance costs and reducing reliability. Thus, current techniques do not allow significant reductions in the number of channels that limits the potential of cost reduction.

Additionally, current THz systems are generally based on passive detection (radiation coming from body itself without being illuminated). Radiation in the millimeter and THz band is weaker than IR radiation and therefore requires higher detector performance and sensitivity with noise equivalent power (NEP) being up to $10^{-12}$ Watt/Hertz$^{1/2}$. Moreover, current THz systems employ detectors based on direct detection principle (sensor directly exposed to the incident radiation) that requires high gain of LNA stages with a flat gain response and gain control of LNA because of oscillations. As noted above, use of expensive LNAs increases the cost of these detectors. Further, known detectors based on indirect detection principles (sensor exposed to parameters that changes based incident radiation), such as helium-cooled bolometers, are costly and have high operating cost.

It is therefore desirable to provide an efficient, reliable, and cost-effective THz detector array working at room temperature for use in a THz inspection or imaging system. It is also desirable to provide an efficient and cost-effective technique for remotely inspecting or imaging a subject using electromagnetic radiation in the THz range.

BRIEF DESCRIPTION

Briefly, in accordance with one aspect of the present technique, a THz inspection or imaging system is provided. The THz inspection system includes a source configured to generate THz radiation and a detector array adapted to detect THz radiation. The detector array is configured to generate a detector output signal in response to THz radiation incident upon the detector by measuring chance in capacitance corresponding to the incident THz radiation.

In accordance with another aspect of the present technique, a detector adapted to detect THz radiation is provided. The detector includes a plurality of detector cells configured to receive the incident THz radiation. Each of the plurality of detector cells further includes an enclosure containing a gas and comprising a flexible membrane having a conductive coating on one side, and a fixed conductive plate facing the metal coating on the flexible membrane to form a variable capacitor. The intensity of the incident radiation corresponds to change in capacitance of the variable capacitor.

In accordance with a further aspect of the present technique, a method is provided for inspecting or imaging a subject. The method provides for illuminating at least a part of the subject with THz radiation and detecting THz radiation reflected and/or transmitted from the illuminated part and incident upon a detector by measuring change in capacitance corresponding to the incident THz radiation.

In accordance with an additional aspect of the present technique, a method is provided for manufacturing a THz detector. The method provides for forming a plurality of enclosure each having a flexible membrane on one side such that each of the plurality of enclosure contains a gas, coating a layer of a conductive material on one side of each of the flexible membrane, and disposing a conductive plate corresponding to each of metal coated flexible membrane at a fixed distance from the flexible membrane.

These and other advantages and features will be more readily understood from the following detailed description of preferred embodiments of the invention that is provided in connection with the accompanying drawings.

DRAWINGS

DETAILED DESCRIPTION

The present techniques are generally directed to a detector array for indirect detection of THz radiation. Generally, these detectors may be used in a variety of THz imaging and/or spectroscopy systems, such as for medical imaging, industrial quality control, and security screening. Though the present discussion provides examples in context of security screening, one of ordinary skill in the art will readily comprehend that the application of these detectors in other contexts, such as for medical imaging and industrial quality control, is well within the scope of the present technique.

It should be noted that reference is made herein to an imaged or scanned "subject". The use of the term is not intended to limit the scope of the appended claims and may broadly indicate a human, an animal, a sealed package, luggage such as a briefcase or a suitcase, a carton, or a cargo container that may be employed to carry an object of interest such as explosives, drugs or weapons. In general, the term may include any article, system, vehicle, or support in which or on which contraband may be placed. Moreover, the subject may refer to objects being examined for a defect via nondestructive evaluation, carrier tissue in a tooth during dental imaging, cancerous tissue in a body during medical imaging, and so forth.

Figure 1:
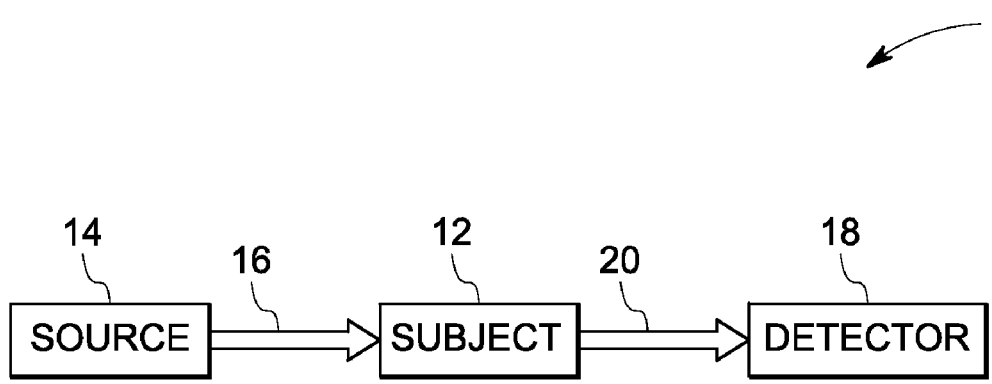
FIGS. 1 and 2 are block diagrams of an exemplary THz inspection or imaging system in accordance with an embodiment of the invention.
Figure 2:
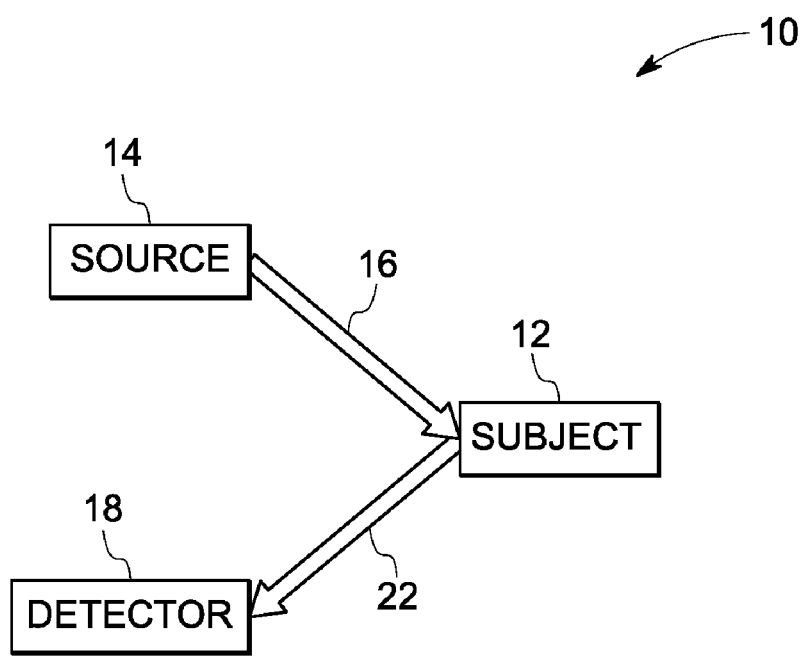

Referring now to FIGS. 1 and 2, a block diagram of an exemplary THz inspection or imaging system 10 is illustrated. The inspection system 10 is configured to examine a subject 12 using electromagnetic radiation in THz range. The inspection system 10 includes a THz source 14 configured to generate the THz radiation for active imaging and/or spectroscopy. In certain embodiments, the generated THz radiation may be in a range of about 0.1 THz to about 10 THz. The source 14 projects the THz radiation 16 toward the subject 12 to be inspected. A THz detector 18 detects the radiation transmitted 20 and/or reflected 22 from the subject 12 and incident upon the detector 18. In certain embodiments, the THz detector 18 may generate a detector output signal in response to the detected THz radiation. The detected THz radiation or the detector output signal may then be reconstructed to generate an image via any known image reconstruction techniques. The generated image may then be analyzed to detect the presence of an object of interest carried by the subject 12. Those skilled in the art will appreciate that the system 10 may be equipped with or connectable to a display unit (not shown) for the display of reconstructed image. Alternatively, the detected THz radiation or the detector output signal may be analyzed to detect the presence of spectroscopic signatures of an object of interest. It should be noted that, in certain embodiments, the object of interest may be contraband concealed on or in the subject 12.

Figure 3:
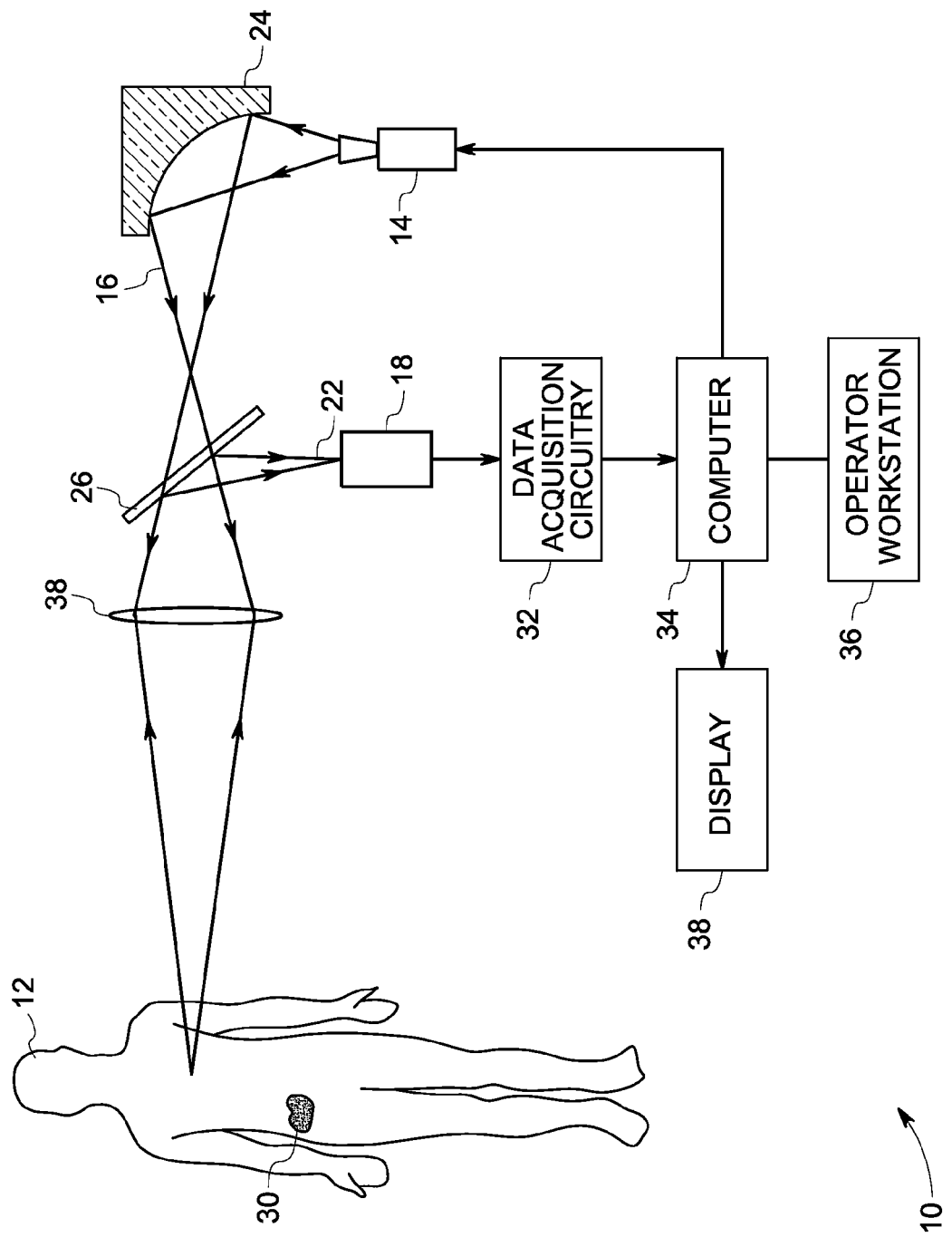
FIG. 3 is a schematic diagram of the THz system of FIG. 2 in accordance with an embodiment of the invention.

A schematic diagram of THz inspection system 10 of FIG. 2 is illustrated in FIG. 3. In the illustrated embodiment, the inspection system 10 includes the THz source 14 configured to generate THz radiation 16 and one or more optical devices configured to illuminate or scan the subject 12 (or a part of the subject 12) with the generated THz radiation 16 by projecting the generated THz radiation 16 on the subject 12. The system 10 further includes the detector 18 configured to detect THz radiation 22 reflected from the subject 12 and generate a detector output signal in response to the detected radiation. The one or more optical devices may include a parabolic mirror 24, a polarizer 26, a lens 28, a beam splitter, a reflecting surface, and so forth to focus the generated THz radiation 16 on the subject 12 and reflected THz radiation 22 on the THz detector 18. As will be appreciated by those skilled in the art, in certain embodiments, the one or more optical devices may be configured to scan the subject along one or more axis by moving along one or more axis. The one or more optical devices are further configured to focus on the subject 12 automatically.

The THz detector 18 is generally formed by a plurality of detector elements or cells, which detect the THz radiation that is transmitted through or reflected from the subject 12. For example, the detector 18 may include multiple rows and/or columns of detector elements arranged in a two-dimensional array. Each detector element, when impacted by the THz radiation, produces an electrical signal (detector output signal) proportional to the absorbed intensity of the incident THz radiation at the position of the individual detector element in detector 18. These signals are acquired and processed to reconstruct an image of the subject and/or detect the presence of an object of interest 30, as described below. In the embodiments discussed herein, indirect detection THz detectors based on acousto-optic principle may be employed to detect the intensity of THz radiation transmitted 20 through and/or reflected 22 from the subject 12 and to generate a detector output signal in response to the detected THz radiation in accordance with aspects of the present technique.

The inspection system 10 may further include data acquisition circuitry 32. In this exemplary embodiment, the detector 18 is coupled to the data acquisition circuitry 32. The data acquisition circuitry 32 receives data collected by readout electronics of the detector 18. In particular, the data acquisition circuitry 32 typically receives sampled analog signals from the detector 18 and converts the data to digital signals for subsequent processing by a computer 34. The computer 34 controls the source 14 and the detector 18. In certain embodiments, the computer 34 activates the source 14, synchronizes the detector 18 with the source 14, and generates a flag and/or an alarm upon detecting the presence of the object of interest 30. The computer 34 may also execute various signal processing and filtration functions, such as for initial adjustment of dynamic ranges, interleaving of digital image data, automatically calibrating the system 10 for image generation and so forth. In general, the computer 34 commands operation of the inspection system 10 to execute inspection protocols and to process acquired data. In the present context, the computer 34 may also include signal-processing circuitry, typically based upon a general purpose or application-specific digital computer, and associated memory circuitry. The associated memory circuitry may store programs and routines executed by the computer, configuration parameters, image data, and so forth. For example, the associated memory circuitry may store programs or routines for reconstructing images from the detector output signal or for otherwise analyzing the detector output signal.

The computer 34 may include a microprocessor, digital signal processor, microcontroller, as well as other devices designed to carry out logic and processing operations. The data collected by the data acquisition circuitry 32 may be transmitted to the computer 34 for subsequent processing and/or reconstruction. For example, the data collected from the detector 18 may undergo pre-processing and calibration at the data acquisition circuitry 32 and/or the computer 34. The processed data may then be used to formulate an image of the imaged area. It should be noted that any suitable reconstruction algorithm may be employed to generate an image from the detector output signal. Once reconstructed, the image produced by the inspection system 10 may be analyzed to detect the presence or absence of the object of interest 30. Alternatively, the processed data may be directly analyzed by the computer 34 to detect the presence or absence of the object of interest 30.

As will be appreciated by those skilled in the art, the computer 34 is configured to detect the presence of the object of interest 30 by detecting the presence of spectroscopic signatures (characteristic reflection and/or absorption spectra) of the object of interest 30 from the detected THz radiation or the detector output signal. For example, in certain embodiments, the object of interest 30 may include an explosive material. The detection of explosive materials is based upon a spectroscopic signature (characteristic absorption and/or reflection spectra) of the explosive material. A wide variety of explosives show strong spectroscopic signatures in the THz range that are distinguishable from other materials, such as human skin. A significant change of the signal indicates with very high probability the presence of explosive materials.

By comparing measured reflective intensity of the reflected THz radiation 22 with the known calibration spectra, the presence of explosives, drugs or other contraband may be identified. As will be appreciated by those skilled in the art, the computer 34 may maintain a look-up table of known explosives and drugs along with their known characteristic reflection and absorption spectra (spectroscopic signatures) in the THz range. The measured reflective intensity will therefore be mapped onto some signature in the look-up table if the respective explosive or drug is present. In other words, the inspection system 10 may use a priori information of explosive materials and/or drugs by their spectral response in the THz regime. Additionally, since metals are relatively opaque to transmission of THz radiation and have a roughly constant reflection spectrum, metal weapons such as handguns and knives may also be identified by THz radiation.

Furthermore, the computer 34 may be configured to receive commands and scanning or imaging parameters from an operator via an operator workstation 36 which may be equipped with a keyboard and/or other input devices. An operator may thereby control the system 10 via the operator workstation 36. Thus, the operator may observe the reconstructed image and other data relevant to the system from operator workstation 36, initiate imaging or scanning, and so forth. A display device 38 coupled to the operator workstation 36 may be utilized to observe the reconstructed image or a raised flag.

The source 14 may be any sweepable ultra-broadband high-power source, such as a backward wave oscillator (BWO) source, a quantum cascading laser (QCL) source, a multiplier chain source, or a gas laser source. As will be appreciated by those skilled in the art, the strong absorption of explosives (e.g., RDX) at about 0.8 THz may be reached with state of the art BWO sources. Moreover, the high power source enables long-range imaging or spectroscopic sensing (remote or standoff detection). In certain embodiments, the source 16 may be configured to generate electromagnetic radiation at continuous frequencies in the THz range. In other words, the source is in continuous tuning mode and the delivered frequency range is large enough to resolve the spectral features of the contraband completely. The specific shape of the measured signal may then be compared with the shape of the known spectral features of contraband to identify them. For example, BWO sources may sweep over a full spectral peek of explosive materials.

Alternatively, the source 14 may be tuned to generate electromagnetic radiation at multiple discrete frequencies in the THz range. In one embodiment, several discrete sources (e.g., QCL sources, multiplier chain sources and so forth) may be employed that may be switched by shutters. The inspection system 10 uses a priori information of sources (the characteristic frequency difference between the sources) to measure expected changes of reflection of the explosives in the signal. Further, each of the multiple discrete frequencies is selected based upon a known spectroscopic signature (characteristic reflection and/or absorption spectra) of the object of interest 14. Thus, the detector 18 measures reflective intensity of the reflected THz radiation 22 at few discrete frequencies close to the spectral signatures of the explosives and drugs. The source 14 therefore behaves as a narrowband source at any particular point of time since it does not generate electromagnetic radiation at continuous frequencies ranging the full spectrum. In other words, the source 14 can sweep specific frequencies such that some of the frequencies correspond to the frequency of explosive signature. By sweeping such specific frequencies, the detector will receive and read these frequencies. Depending upon the type of explosives or drugs carried by the subject 12, the explosive or drug may appear at certain frequencies and may not appear at other frequencies. Thus, the reflective/transmissive intensity measurement is done for an entire region of the subject or a region within the subject 12 towards which a selected narrow bandwidth of radiation is directed or focused.

As will be appreciated by those skilled in the art, the one or more optical devices is configured to scan or illuminate the subject 12 at each of the selected multiple frequencies. It should be noted that scanning the subject 12 may be done in various ways. In certain embodiments, the entire subject 12 may be scanned or illuminated at one selected frequency and then with a next selected frequency. Alternatively, in certain embodiments each region of the subject 12 is scanned at multiple frequencies before moving to a next region.

Figure 4:
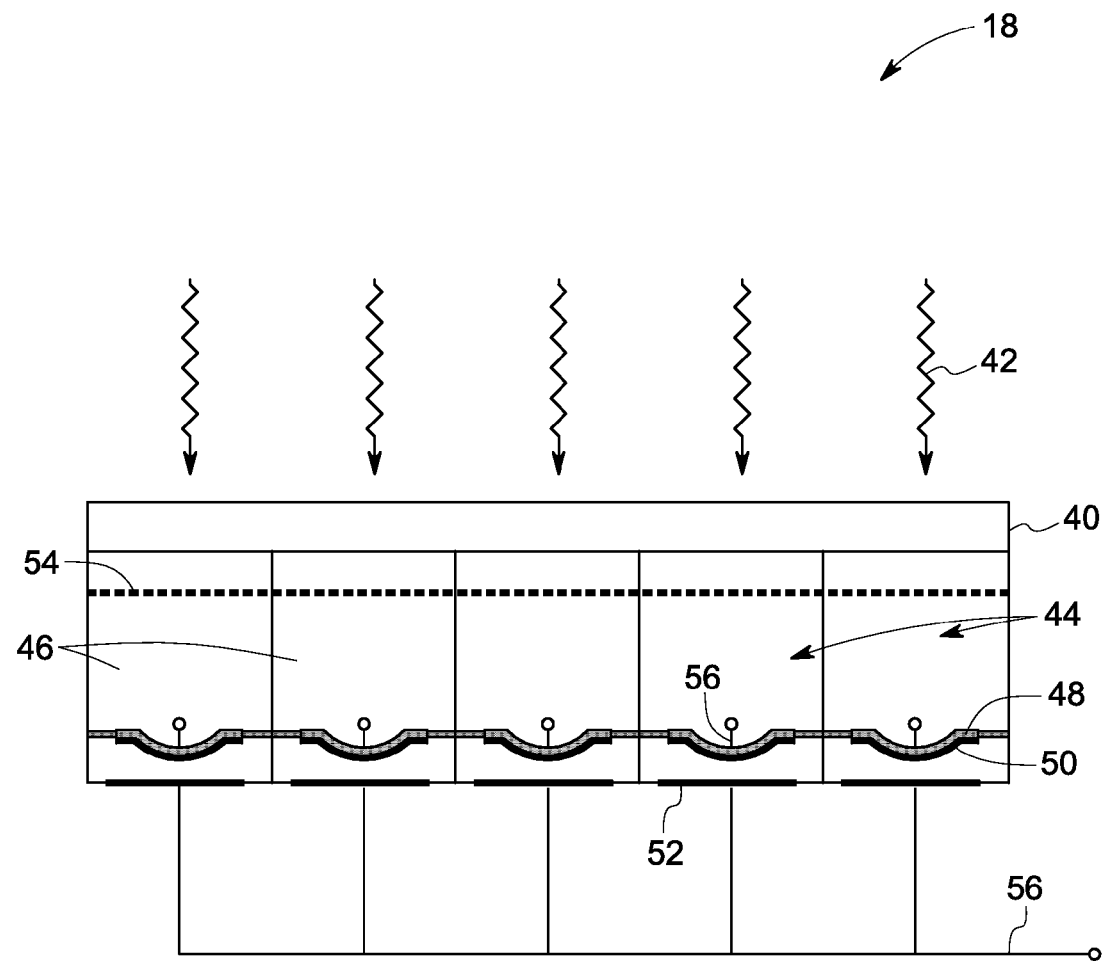
FIG. 4 is a schematic diagram of a THz detector for use in a THz system of FIGS. 1-3 in accordance with an embodiment of the invention.

The exemplary inspection system 10, as well as other inspection systems based on THz radiation detection, employs a THz detector 18 to detect the intensity of incident THz radiation and to generate a detector output signal in response to the detected THz radiation. For example, in certain embodiments, indirect broadband detectors, such as Golay cell broadband detectors, cryogenically cooled bolometers (e.g., helium cooled silicon bolometers), antennae coupled bolometers, pyroelectric broadband detectors, and the like, may be employed by the exemplary inspection system 10. These detectors permit THz imaging and/or spectroscopy with ultra broadband sensitivity. A schematic diagram of an exemplary indirect THz detector 18 is depicted in FIG. 4 in accordance with aspects of the present technique. The exemplary indirect THz detector 18 is a two-dimensional broadband detector array based on an acousto-optical principle detecting the intensity of THz radiation by measuring a capacitive change of a plurality of variable capacitors integrated within the THz detector 18 as illustrated in FIG. 4.

The detector 18 generally includes an entrance window 40 for receiving THz radiation 42. It should be noted that the entrance window 40 may be made of any material transparent to the THz radiation, such as glass or ceramic. The detector further includes a plurality of detector cells (elements) 44 arranged in a two-dimensional array and configured to receive incident THz radiation 42 through the entrance window 40. Each of the plurality of detector cells 44 includes an enclosure 46 (closed chamber) containing a gas. The gas may be air, nitrogen, an ideal gas (e.g., helium), or any other suitable gas or a gas mixture. The enclosure 46 is bounded by a thin flexible membrane 48 on one of the sides (e.g., the bottom side of the detector cell). The flexible membrane 48 may be a silicon membrane. The flexible membrane 48 has an electrically conductive (e.g., metal) coating 50 on the outer side (side away from the enclosure 46. The detector cell 44 further includes a fixed electrically conductive (e.g., metal) plate 52 facing the conductive coating 50 on the flexible membrane 48 so as to form a variable capacitor. The conductive coating 50 and the conductive plate 52 forms two electrodes of the variable capacitor. Each of the detector cells 44 further includes a layer of absorbent 54 disposed within the enclosure 46 for effectively absorbing the incident THz radiation and heating the surrounding gas. It should be noted that the material and geometry of the absorbent layer, the used gas and/or the geometry of the variable capacitor may be optimized for the THz detector based on the required sensitivity and other requirements. As will be appreciated by those skilled in the art, temperature changes induced by the absorbed photons in one cell may result in signal changes in the neighboring cells and hence may reduce the ability to correctly decode the interaction position of the THz radiation 42. Each of the detector cells 44 may therefore be made of heat insulating (non-thermal) material so that the heat is trapped within the respective cells 44. The detector array 18 may be fabricated using micro-electro-mechanical systems (MEMS) chips. In certain embodiments, silicon MEMS chips may be employed by the present technique. Based on the standard MEMS processing, the array could be fabricated at substantially lower cost. Moreover, the MEMS technology makes the each of the detector cells small enough to correspond to each pixel in the reconstructed image.

The gas upon receiving the THz radiation expands and exerts pressure on the thin flexible membrane causing the flexible membrane to bend, thereby changing the capacitance of the variable capacitor. The change in capacitance of the variable capacitors is proportional to the expansion of the gas, which in turn is proportional to the intensity of the incident THz radiation. The change in capacitance is therefore proportional to the overall THz intensity. As will be appreciated by those skilled in the art, the gas within the enclosure 46 expands proportionally to the energy and the amount of the THz radiation absorbed. As such, expansion will be higher in those detector cells where either more THz radiation was received or the energy level of the received THz radiation was higher. Since the intensity of the transmitted and/or reflected THz radiation will vary, the energy level and the amount of the THz radiation impinging upon the detector cells will not be uniform across the detector array. This variation in intensity will be used to generate contrast in the reconstructed image and/or detect the presence or absence of the object of interest. The variable capacitors therefore store electrical charge in proportion to the quantity of incident light absorbed by each detector cells.

Those skilled in the art will appreciate that as compared to generally similar detectors based on acousto-optical principles that typically detect radiation in the infrared range and not in the THz range, the detector illustrated in FIG. 4 is adapted to detect THz radiation. Indeed, those skilled in the art will find that remotely similar structures could be used for successful THz inspection or imaging. This is enabled, in part, by modifying the dimensions of each of the detector cells 44. For example, for the same level of sensitivity, each of the detector cells of the described THz detector 18 is smaller but deeper in comparison to that of infrared detectors based on acousto-optical principles. This enables the detector cells to detect THz radiation with substantially equivalent sensitivity. For example, in certain embodiments, the length of the side receiving the THz radiation (the side adjacent to the entrance window) of the detector cell 44 is about 100 micrometers, while that of existing infrared detectors is about 1 millimeter. Thus, each of the detector cells contributes towards a pixel in the reconstructed image.

The THz detector 18 may further include read-out electronics 56 coupled to the electrodes of the variable capacitors for reading the change in capacitance or the electrical charge of each of the variable capacitors and generating an electrical signal (detector output signal) proportional to the electrical charge for each of the variable capacitors. Thus, each detector element has a THz radiation reception region that absorbs light and subsequently creates and stores electronic charge and a region comprising of electronics to control the storage and output of electrical charge from that detector element. After exposure, the electrical charge in each detector element is read out using logic-controlled electronics (e.g., CMOS, transistors and so forth). By analyzing these electrical signals, the intensity of the incident THz radiation is determined for subsequent processing.

In certain embodiments, each detector element is generally controlled using a transistor-based switch. In this regard, the source of the transistor is connected to one plate of the variable capacitor, the drain of the transistor is connected to a readout line, and the gate of the transistor is connected to a scan control interface disposed on the readout electronics 56. When negative voltage is applied to the gate, the switch is driven to an OFF state, thereby preventing conduction between the source and the drain. Conversely, when a positive voltage is applied to the gate, the switch is turned ON, thereby allowing charge stored in the variable capacitor to pass from the source to the drain and onto the readout line. Each detector element of the detector array is constructed with a respective transistor and is controlled in a manner consistent with that described below.

Specifically, during exposure to THz radiation, negative voltage is applied to all gate lines resulting in all the transistor switches being driven to or placed in an OFF state. As a result, any charge accumulated during exposure is stored in the variable capacitor of each detector element. During read out, positive voltage is sequentially applied to each gate line, one gate line at a time. That is, the detector is an X-Y matrix of detector elements and all of the gates of the transistors in a line are connected together so that turning ON one gate line simultaneously reads out all the detector elements in that line. In this regard, only one detector line is read out at a time. A multiplexer may also be used to support read out of the detector elements in a raster fashion. An advantage of sequentially reading out each detector element individually is that the charge from one detector element does not pass through any other detector elements. The output of each detector element is then input to an output circuit (e.g., a digitizer) that digitizes the acquired signals for subsequent image reconstruction on a per pixel basis or for subsequent analysis. Each pixel of the reconstructed image corresponds to a single detector element of the detector array. It should be noted that the one or more components described here may be a part of detector itself or of the data acquisition circuitry.

Figure 5:
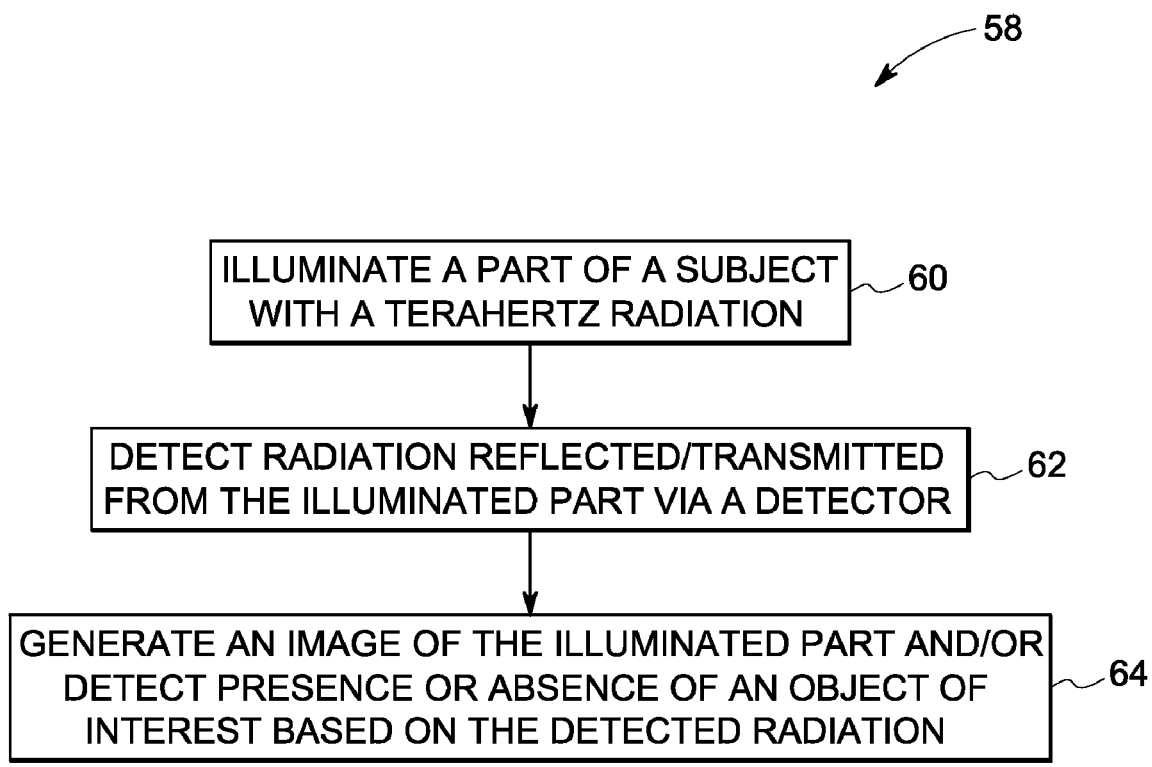
FIG. 5 depicts a control scheme for inspecting or imaging a subject via a THz system of FIGS. 1-3 in accordance with an embodiment of the invention.

A control scheme 58 for examining (inspecting or imaging) a subject via the THz inspection system of FIGS. 1-3 in accordance with an embodiment of the invention is illustrated in FIG. 5. The control scheme 58 includes illuminating a part of the subject 12 with THz radiation at step 60, detecting the THz radiation reflected or transmitted from the illuminated part via a THz detector at step 62, and generating an image of the illuminated part and/or detecting presence or absence of the object of interest based on the detected radiation at step 64. As will be appreciated by those skilled in the art, the THz detector is configured to measure the intensity of the incident radiation by measuring change in the capacitance corresponding to the incident radiation.

The two-dimensional detector array for THz detection described in the various embodiments discussed herein is an efficient, reliable, and cost-effective detector for use in a THz inspection system based on imaging as well as spectroscopy. The indirect detection avoids usage of expensive MMIC technology, thereby providing significant cost reduction. Use of active source reduces the requirement on detector sensitivity by a factor of about 10. Thus, the use of active indirect detection leads to cost optimization. Moreover, the use of two-dimensional detector array minimizes the need of mechanical scanning and enables near real time imaging (video-rate imaging) or spectroscopy, thereby increasing throughput and decreasing the inconvenience caused during screening. The detectors further have reduced maintenance cost and increased reliability, as no mechanical scanning is needed. Additionally, the THz detector described herein enables camera like operation for photographing the subject using THz radiation. Moreover, the detector described in various embodiments discussed above is capable of detecting various THz frequencies, thereby enabling hyper-spectral or multi-spectral imaging applications.

The use of standard Si-MEMS fabrication processes enables cost efficient fabrication of THz detectors, thereby achieving significant cost reduction. A noise equivalent power (NEP) of up to $10^{-11}$ Watt/Hertz$^{1/2}$ may be achievable. Further, the ultra-broadband sensitivity allows the use of these detectors in the infrared range. Additionally, acousto-optical detectors with capacitive read-out may be employed for applications where high sensitivity is required, such as for radiometer technology for passive THz detection. Moreover, the detectors may be employed for other applications such as medical imaging, quality inspection (e.g., non destructive evaluation) and so forth.

The active THz inspection system based on an indirect detection principle described herein employs high power source for active illumination, thereby avoiding the use of sensitive detectors and mechanical scanning. Thus the system is cost effective, reliable and compact. Additionally, the use of a high power source enables standoff detection (long range detection) and use of reduced detection sensitivity detectors. This leads to a significant reduction of system costs. The reduced number of optical elements as well as use of conventional low-cost optical elements further provides significant cost advantage. Such techniques may be useful in a variety of applications that require efficient, reliable, cost-effective, and rapid screening/inspection of persons, luggage, packages or cargo using THz radiation.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A terahertz (THz) inspection or imaging system, comprising:
   an electromagnetic radiation source configured to generate electromagnetic radiation at multiple discrete frequencies in the THz range; and
   a detector array including a plurality of detector cells adapted to detect THz radiation, each of the plurality of detector cells comprising a gas-filled variable capacitor and configured to generate a detector output signal in response to a change in capacitance in the variable capacitor caused by thermal expansion of the gas, the change in capacitance corresponding to an intensity of the THz radiation incident upon the integrated detector cell.

2. The system of claim 1, wherein the electromagnetic radiation source comprises a broadband electromagnetic radiation source and wherein the detector array comprises a two-dimensional broadband detector array.

3. The system of claim 1, wherein the radiation source comprises a backward wave oscillator source, a quantum cascading laser source, a multiplier chain source, a gas laser source, or other high-power source.

4. The system of claim 1, wherein each of the multiple discrete frequencies is selected based upon a known spectroscopic signature of an object of interest.

5. The system of claim 1, comprising one or more optical devices configured to illuminate at least a part of a subject with the generated THz radiation.

6. The system of claim 5, wherein the detector array is configured to detect THz radiation reflected and/or transmitted from the illuminated part.

7. The system of claim 5, wherein the one or more optical devices are configured to focus on the illuminated part of the subject automatically.

8. The system of claim 1, comprising a processor configured to at least one of:
   generate an image based upon the detector output signal;
   identify the presence or absence of an object of interest within the generated image; and
   automatically calibrate the THz inspection or imaging system.

9. The system of claim 1, comprising a processor configured to detect the presence or absence of an object of interest based upon the detector output signal.

10. The system of claim 9, wherein the processor is configured to detect the presence of the object of interest by detecting the presence of a spectroscopic signature of the object of interest from the detector output signal.

11. The system of claim 1, wherein the THz radiation is in a range of about 0.1 THz to about 10 THz.

12. The system of claim 1, wherein the electromagnetic radiation source generates a selected narrow bandwidth of THz radiation at any particular point of time rather than generating electromagnetic radiation at continuous frequencies ranging a full spectrum.

13. The system of claim 1, wherein the detector array detects an intensity of a broad bandwidth of incident THz radiation.

14. A detector adapted to detect terahertz (THz) radiation, the detector comprising:
a plurality of detector cells arranged in an array and configured to receive the incident THz radiation, each of the plurality of detector cells comprising:
an enclosure containing a gas and comprising a flexible membrane having a conductive coating on one side; and
a fixed conductive plate facing the conductive coating on the flexible membrane to form a variable capacitor, wherein intensity of the incident radiation corresponds to a change in capacitance of the variable capacitor.

15. The detector of claim 14, wherein the gas expands and exerts pressure on the flexible membrane upon receiving the incident radiation causing capacitance of the variable capacitor to change by bending the flexible membrane.

16. The detector of claim 14, comprising a layer of absorbent disposed within the enclosure for absorbing the incident radiation and heating the surrounding gas.

17. The detector of claim 14, comprising an entrance window for receiving the incident radiation.

18. The detector of claim 17, wherein the entrance window comprises a material transparent to THz radiation.

19. The detector of claim 14, comprising readout circuitry coupled to the plurality of variable capacitors for measuring change in capacitance of each of the plurality of variable capacitors and generating a detector output signal.

20. The detector of claim 14, wherein the enclosure includes a heat insulating material configured to prevent a temperature change within a first detector cell of the plurality of detector cells from effecting a second detector cell of the plurality of detector cells.

21. A method of inspecting or imaging a subject, comprising:
illuminating at least a part of the subject with a terahertz (THz) radiation of a first selected frequency;
detecting THz radiation reflected and/or transmitted from the illuminated part in response to the THz radiation of the first selected frequency at a detector array; and
generating a detector output signal in response to a change in capacitance in a variable capacitor of the detector array caused by thermal expansion of a gas included within the detector array, the change in capacitance corresponding to the THz radiation incident upon the detector array.

22. The method of claim 21, further comprising generating the THz radiation.

23. The method of claim 21, comprising generating an image of the illuminated part based upon the detected THz radiation.

24. The method of claim 23, comprising identifying the presence or absence of an object of interest within the generated image.

25. The method of claim 21, comprising detecting the presence or absence of an object of interest based upon the detected THz radiation by detecting the presence or absence of a spectroscopic signature of the object of interest from the detected THz radiation.

26. The method of claim 21 further comprising:
illuminating at least a part of the subject with a THz radiation of a second selected frequency; and
detecting THz radiation reflected and/or transmitted from the illuminated part in response to the THz radiation of the second selected frequency at the integrated detector array.

27. A method of manufacturing a terahertz (THz) detector, the method comprising:
forming a plurality of enclosures using microelectromechanical system (MEMS) techniques, each enclosure having a flexible membrane on one side such that each of the plurality of enclosures contains a gas;
coating a layer of a conductive material on one side of each of the flexible membrane membranes; and
disposing a conductive plate corresponding to each of the coated flexible membranes at a fixed distance from the flexible membrane to form a gas-filled variable capacitor, wherein an intensity of incident radiation corresponds to a change in capacitance of the variable capacitor.

28. The method of claim 27, comprising disposing a layer of absorbent within each of the plurality of enclosures.

29. The method of claim 27, comprising coupling an entrance window to the plurality of enclosures to receive the incident THz radiation.

30. The method of claim 27, comprising electrically coupling a readout circuitry to the plurality of conductive plates and conductive coatings.

31. The method of claim 27, wherein the plurality of enclosures include a heat insulating material configured to trap heat within each enclosure and to prevent a temperature change within a first enclosure of the plurality of enclosures from affecting a second enclosure of the plurality of enclosures.

* * * * *